United States Patent [19]

Cowan

[11] 4,208,404

[45] Jun. 17, 1980

[54] GLUTARALDEHYDE STERILIZING COMPOSITIONS

[76] Inventor: Stanley M. Cowan, 1947 Mattawa Ave., Mississauga, Ontario, Canada

[21] Appl. No.: 953,352

[22] Filed: Oct. 23, 1978

Related U.S. Application Data

[63] Continuation-in-part of Ser. No. 861,199, Dec. 16, 1977, abandoned, which is a continuation of Ser. No. 492,884, Jul. 29, 1974, abandoned.

[51] Int. Cl.² .................. A01N 11/00; A01N 9/00; A01N 9/24
[52] U.S. Cl. .................... 424/153; 424/166; 424/317; 424/333
[58] Field of Search ............. 424/333, 166, 317, 153

[56] References Cited

U.S. PATENT DOCUMENTS

| 3,282,775 | 11/1966 | Stonehill | 424/333 |
| 3,697,222 | 10/1972 | Sierra | 424/333 |
| 3,912,450 | 10/1975 | Boucher | 424/333 |

FOREIGN PATENT DOCUMENTS

1052537  12/1966  United Kingdom ............... 424/333

OTHER PUBLICATIONS

Remington's Pharm. Sciences, 13th Ed., 1965, pp. 242–243.
J. Bacteriol, 86, 207–211 (1963), Voss.
Preprint of Scientific Papers, The 6th Congress on the Nat. Fed. of Societies of Cosmetic Chemists, vol. II, pp. 836–850 (1970).
"Inhibition and Destruction of the Microbiol Cell", Hugo (ED), Academic Press (1971), pp. 270–271, 280, 477, 482–484, 498–499, 528, 563–564, 570–572, and 725–728.

*Primary Examiner*—Douglas W. Robinson
*Attorney, Agent, or Firm*—Sim & McBurney

[57] ABSTRACT

Aqueous solutions of glutaraldehyde of acid pH value contain dissolved quantities of certain highly ionized salts and have the ability to kill dormant spores at room temperature.

10 Claims, No Drawings

GLUTARALDEHYDE STERILIZING COMPOSITIONS

REFERENCE TO RELATED APPLICATION

This application is a continuation-in-part of application Ser. No. 861,199 filed Dec. 16, 1977 now abandoned which itself is a continuation of application Ser. No. 492,884 filed July 29, 1974 (now abandoned).

FIELD OF INVENTION

This invention relates to sterilizing compositions, and more particularly to sterilizing compositions having efficient sporicidal activity at room temperature and to sterilizing processes utilizing the same.

BACKGROUND OF THE INVENTION

Sterilants are used in many areas, such as in the sterilization of laboratory, surgical, dental and other equipment. It is convenient in hospital practice to sterilize instruments overnight, using chemical sterilizing agents or other sterilizing methods.

The most common methods of sterilization involve either the use of steam under pressure, dry heat or ethylene oxide. However, some of these methods can be cumbersome, tedious and time-consuming, often damage the sterilized material and require expensive equipment and skilled technicians.

The power of a chemical sterilizing agent is best measured by its ability to kill sporulating bacteria, while many disinfectants can kill vegetative bacteria, very few are capable of killing dormant spores, such as *Bacillus subtilis, Bacillus pumilus, Clostridium sporogenes* and *Clostridium tetani.*

The term "sterilizing composition" as used herein is intended to refer to compositions which are capable of killing dormant spores in addition to vegetative bacteria while the term "sterilizing" refers to the killing of dormant spores.

Some activity in the search for a more effective and convenient sterilizing procedure has been centered around the use of glutaraldehyde as the basis for chemical sterilant compositions.

Commercially-available glutaraldehyde is in the form of an acidic aqueous solution which is stable over long periods of time. However, these solutions do not exhibit the ability to kill dormant spores at room temperature (i.e., 20° to 25° C.) within an acceptable period of time, i.e., less than 16 hours (a period of time equivalent to an overnight treatment) and for even longer periods in excess of 24 hours. This acidic solution cannot therefore, be used as is as a sterilant composition.

U.S. Pat. No. 3,016,328 issued Jan. 9, 1962 to Rollin E. Pepper et al and assigned to Ethicon, Inc., discloses a sterilizing agent which is an aqueous solution of glutaraldehyde having an alkaline pH, generally around 7.5 to 8.0. This alkaline composition is effective in killing dormant spores at temperatures of around 20° to 25° C. in treatment periods of from 3 to 10 hours to achieve complete deactivation depending on the state and resistance of the spores.

While acid aqueous solutions of glutaraldehyde are stable and have long shelf life, alkaline solutions by contrast tend to lose their sporicidal activity rapidly upon storage, as a result, it is thought, of alkaline catalyzed polymerization of the glutaraldehyde. This latter defect has lead to the marketing of the product in the form of an aqueous acid solution of glutaraldehyde together with a separate container of solid alkali, such as, sodium bicarbonate, the alkali being added to the acid solution just prior to use to provide the required alkaline pH.

This procedure gives rise to several problems. Thus, the container of alkali may become detached from the container of aqueous glutaraldehyde. Alternatively, the addition of alkali may be accidentally omitted by the user. In either case, this leads to the use of a solution known to be ineffective at 20° to 25° C. in an acceptable period of time (i.e., less than 16 hours).

In view of the prior art problems associated with the use of alkaline glutaraldehyde solutions, various prior attempts have been made to provide acid glutaraldehyde solutions having sporicidal activity and thereby take advantage of the stable nature of acid glutaraldehyde.

For example, U.S. Pat. No. 3,282,775 (Stonehill) describes glutaraldehyde compositions including acid glutaraldehyde compositions, containing cationic surfactants and U.S. Pat. No. 3,912,450 (Boucher) describes acid glutaraldehyde compositions containing certain non-ionic surfactants.

Further, in U.S. Pat. No. 3,647,222 (Sierra), it is suggested to heat acid glutaraldehyde to a temperature above about 45° C. or to effect sterilization using acid glutaraldehyde solution in the presence of ultrasonic energy both at ambient and elevated temperatures.

SUMMARY OF INVENTION

The present invention provides an acid glutaraldehyde solution (i.e., one having a pH of less than 7), which is capable of killing dormant spores at room temperature (20° to 25° C.) in an acceptable period of time (as defined above), and which does not use any of the prior art techniques discussed above. Thus, the compositions used in this invention to be sporicidally effective, do not require the presence of either cationic or non-ionic surfactants, as suggested by Stonehill and Boucher, and the sterilizing process need not be effected at temperatures above 45° C. or in the presence of ultrasonic energy, as suggested by Sierra.

The ability to effect room temperature sterilization using a solution which does not require mixing immediately prior to use is of considerable benefit when compared with the prior art use of alkaline glutaraldehyde by Pepper et al and the prior art use of elevated temperatures and/or ultrasonic energy by Sierra.

Further, as will become apparent hereinafter, the compositions used in this invention contain additives of considerably lower cost than the surfactants used in the Stonehill and Boucher compositions.

In accordance with the present invention, a highly ionizable salt, that is, a salt which is wholly or substantially dissociated into its component ions in an aqueous medium, is dissolved in an acid aqueous solution of glutaraldehyde in an amount effective to impart the ability to kill dormant spores to the aqueous solution in an acceptable period of time, as determined at 20° to 25° C. This composition is utilized to kill dormant spores over a wide range of temperatures from 15° C. up to the boiling point of the composition.

GENERAL DESCRIPTION OF INVENTION

The compositions used in this invention have an acid pH value, i.e., a pH value less than 7 and a lower limit of pH of 2. The compositions generally have a pH value in the range of 3 to 6.5, preferably 4.5 to 5.5.

The aqueous solvent used in the composition may be provided wholly by water or by an aqueous solution of water and a lower alkanol, such as, isopropanol. The proportion of alcohol present may vary widely and depends to a certain extent on the solubility of the desired highly ionized salt in the aqueous alcoholic solution.

The compositions used in this invention may be made up in a concentrated form which is diluted for use. The proportions of the components of the composition enumerated herein refer to the composition as used and not to a concentrate thereof.

The concentration of glutaraldehyde in the composition as used may vary widely from 0.5 to 10% by weight, although quantities of about 1 to 2% by weight usually are preferred. As mentioned above, aqueous glutaraldehyde compositions having the above-noted acid pH values in the absence of any additives thereto do not kill dormant spores at room temperature (20° to 25° C.) in an acceptable period of time, i.e., less than 16 hours and typically in a much longer period of time.

In accordance with this invention, at least one highly ionizable salt of a specified type is dissolved in the aqueous glutaraldehyde composition in sufficient quantity to impart thereto the ability to kill dormant spores at room temperature in an acceptable period of time, i.e., less than 16 hours, preferably less than 12 hours and more preferably less than 10 hours.

The salts which are used in this invention include neutral lithium, sodium, potassium and ammonium salts of the inorganic acids, sulphuric acid, hydrochloric acid or nitric acid or the organic acids, citric acid or acetic acid. Mixtures of two or more salts may be used.

In the Stonehill patent, alkaline pH values are specified as well as acid ones and it is indicated that various additives and buffers may be used to achieve alkalination. Certain of the neutral salts used in this invention are known for use in buffering systems, i.e., systems in which a salt of a weak base and a strong acid in combination with the weak base, for example, the combination of ammonium chloride and ammonium hydroxide (for buffering in the alkali range), or a salt of a strong base and a weak acid in combination with the weak acid, for example, sodium acetate and acetic acid (for buffering in the acid range), are used to control variations in pH upon addition of acid or base to the system.

However, in the present invention, the salts alone are used and not in a buffering combination with the appropriate acid. As an example, ammonium chloride may be used in this invention but only acts as a buffer in alkaline media also containing ammonium hydroxide.

Representative examples of suitable salts include sodium chloride, ammonium chloride, lithium chloride, potassium chloride, sodium nitrate, potassium nitrate, sodium sulphate, potassium sulphate, sodium citrate, sodium acetate, and mixtures of sodium chloride and sodium nitrate, and sodium chloride and potassium nitrate.

The quantity of highly-ionizable salt utilized may vary from a minimum of that providing the desired room temperature sporicidal acitivity, which in turn is dependent on the number of spores present, generally about 0.01% by weight up to saturation of the aqueous glutaraldehyde solution by the salt. Preferably, total quantities of about 0.5 to about 1.0% by weight of highly ionizable salt are used.

While the killing of dormant spores may be effected at room temperature using an acid glutaraldehyde composition, thereby providing a versatility not possessed by prior glutaraldehyde-based sterilization procedures, mildly elevated temperatures below 45° C. may be used to accelerate the sterilization process.

If desired, temperatures above 45° C. and up to the boiling point of the aqueous composition may be employed, but these are less preferred.

The compositions used in this invention kill the dormant spores at room temperature without germination of the spores. Phase contrast illumination of the spores as observed through an optical microscope shows the spores as phase bright both before and after treatment. Under the same illumination conditions, germinated spores show as phase dark, so that the fact that the spores after treatment retain their spore form demonstrates that germination does not occur during the room temperature treatment.

EXAMPLES

Example I

Several aqueous glutaraldehyde compositions were prepared and their effectiveness was measured in killing hydrated ungerminated (dormant) spores of Bacillus subtilis ATCC 6051 at spore loadings of $1 \times 10^8$ at 20° to 25° C. over a four hour period. Two percent aqueous glutaraldehyde solutions were tested and the salt additives were present in a quantity of 0.7% w/v in each case.

In this testing procedure, the spores were observed through an optical microscope under phase contrast illumination both prior to and after glutaraldehyde treatment. The spores showed phase bright in both instances, so that the spores had retained their spore character and had not germinated during the glutaraldehyde treatment. Any germination of the spores would have shown up phase dark in the optical microscope.

Following the glutaraldehyde treatment, the spores were placed in a nutrient germination medium and the degree of germination of the spores was determined to test the degree of kill attained by the various compositions during the test period.

The results are reproduced in the following Table I:

TABLE I

| Additive to glutaraldehyde solution | pH | Sporicidal Activity at 4 hours |
|---|---|---|
| Sodium Chloride | 3.7 | Complete kill |
| Lithium Chloride | 3.7 | Complete kill |
| Sodium Nitrate | 3.7 | Complete kill |
| Ammonium Chloride | 3.5 | Complete kill |
| Sodium Citrate | 6.9 | Complete kill |
| Potassium Chloride | 3.6 | Complete kill |
| Potassium Nitrate | 3.7 | Complete kill |
| Sodium Chloride and Sodium Nitrate (50:50w/w) | 3.7 | Complete kill |
| Sodium Chloride and Potassium Nitrate | 3.7 | Complete Kill |
| No additives | 3.5 | 100% germination |
|  | 3.6 | 100% germination |
|  | 3.7 | 100% germination |

The results of Table I show that aqueous glutaraldehyde solutions having an acid pH and containing certain dissolved highly ionized salts are more effective sporidical compositions than glutaraldehyde alone.

Example II

Further aqueous glutaraldehyde compositions were prepared and their effectiveness was measured in killing hydrated ungerminated (dormant) spores of *Bacillus Subtilis* ATCC 6051 at spore loadings of $1 \times 10^8$ at 20° to 25° C. over various time periods. Two percent aqueous glutaraldehyde compositions were tested and the salt additives were present in a quantity of 0.7% w/v in each case.

Optical microscopic examination of the pores was effected as described in Example I and subsequent manipulation of the spores also was as described in Example I. The results are reproduced in the following Table II:

TABLE II

| Additive to glutaraldehyde Solution | pH | Sporicidal Activity 4 | 8 | 16 hrs. |
|---|---|---|---|---|
| Potassium sulphate | 3.7 | 40% germination | complete kill | — |
| Sodium sulphate | 3.7 | 30% germination | complete kill | — |
| Sodium acetate | 6.1 | 40% germination | complete kill | — |
| Magnesium chloride | 3.3 | 50% germination | — | complete kill |
| Sodium dihydrogen phosphate | 4.2 | 50% germination | — | complete kill |
| Potassium dihydrogen phosphate | 4.2 | 80% germination | — | complete kill |

The results of the above Table II illustrate that certain salts impart a less rapid sporicidal action to the glutaraldehyde solution, and, in the cases of magnesium chloride and sodium and potassium dihydrogen phosphate, the treatment time for complete kill is considered too long to be effective.

Example III

The procedure of Example I was repeated comparing the sporicidal activity of a composition of the invention at elevated temperatures below 45° C. with that of acid glutaraldehyde alone. The results are reproduced in the following Table III:

TABLE III

| Additive to glutaraldehyde solution | pH | Temperature | Sporicidal Activity |
|---|---|---|---|
| Sodium chloride | 3.7 | 27° C. | Complete kill at 2¼ hours |
| Sodium chloride | 3.7 | 37° C. | Complete kill at 1 hour |
| No additive | 3.5 | 37° C. | Complete kill at 20 hours |

The results of Table III indicate the increased sporicidal activity of a composition of the present invention at an elevated temperature, as compared with acid aqueous glutaraldehyde.

Example IV

This Example is intended to illustrate the effectiveness of the composition under the A.O.A.C. dried spore sporicidal test conditions as modified by E.P.A.

Porcelain ring and silk suture loop carriers were prepared and contaminated with spore cultures of *B. subtilis* and *Cl. sporogenes*, at a minimum spore load of $1 \times 10^7$ per carrier. The carriers were vacuum dried and had a minimum resistance to 2.5 N HCl at 20° C. as follows (the AOAC test minimum being 2 mins.):

*B. Subtilis:* 10 mins.
*Cl. sporogenes:* 15 mins.

The carrier was then immersed in an aqueous glutaraldehyde solution containing 0.7% by weight of sodium chloride having a pH of 5.0 and containing 2% by weight of glutaraldehyde for a test period at a test temperature. Following contact with the glutaraldehyde solution, each carrier was passed through a neutralizing medium and transferred to an incubation medium. The tubes were incubated for 21 days, and after heat shocking at 80° C., the tubes were reincubated for 72 hours.

The results obtained for sets of 60 carriers are set forth in the following Table IV:

TABLE IV

| A. Culture | *B.subtilis* (ATCC 19659) | | | |
|---|---|---|---|---|
| Carrier | Loops | | Rings | |
| Temperature | 20° C. | 37° C. | 20° C. | 37° C. |
| Average Exposure time for 100% kill | 8 hrs | 2 hrs | 8 hrs | 1½ hrs |
| B. Culture | *Cl. sporogenes* (ATCC 3584) | | | |
| Carrier | Loops | | Rings | |
| Termperature | 20° C. | 37° C. | 20° C. | 37° C. |
| Average exposure time for 100% kill | 10 hrs | 2 hrs | 9½ hrs | 2 hrs |

The above results indicate that the composition met the A.O.A.C. requirements.

SUMMARY OF DISCLOSURE

The present invention, therefore, provides a sterilizing composition based on aqueous glutaraldehyde which is effective at room temperature or above in the acid pH range and a sterilizing procedure based on such composition.

Modifications are possible within the scope of the invention.

What I claim is:

1. A method of killing dormant spores, which consists of contacting said spores with a sporicidally-effective amount of a liquid sterilizing composition having a pH from about 2 to less than 7 at a temperature of about 15° C. up to the boiling point of the composition,
said sterilizing composition consisting of:
a solvent selected from water and a mixture of water and a lower alkanol,
0.05 to 10% by weight of glutaraldehyde, and
at least 0.01% by weight up to saturation of the composition thereby of at least one highly ionizable neutral salt dissolved in the solvent and selected from the group consisting of lithium, sodium, potassium and ammonium salts of sulphuric acid, hydrochloric acid, nitric acid, citric acid or acetic acid, or mixtures thereof.

2. The method of claim 1 wherein said composition has a pH of 3 to 6.5.

3. The method of claim 2, wherein said composition has a pH of 4.5 to 5.5.

4. The method of claim 1 wherein said glutaraldehyde concentration is 1 to 2% by weight.

5. The method of claim 1 effected at a temperature of about 20° to 25° C.

6. The method of claim 1 wherein said highly ionizable salt concentration is 0.5 to 1% by weight.

7. The method of claim 1 effected at a temperature of 20° to 25° C. and wherein said composition has a pH of 3 to 6.5, the glutaraldehyde has a concentration of 1 to 2% by weight and the highly ionizable salt concentration is 0.5 to 1% by weight.

8. The method of claim 7 wherein said at least one highly ionizable salt is selected from the group consisting of sodium chloride, ammonium chloride, lithium chloride, potassium chloride, sodium nitrate, potassium nitrate, sodium sulphate, potassium sulphate, sodium citrate, sodium acetate and mixtures of sodium chloride and sodium nitrate and sodium chloride and potassium nitrate.

9. The method of claim 7 wherein said at least one highly-ionizable salt is sodium chloride and said pH is 4.5 to 5.5.

10. The method of claim 1 including diluting a concentrated form of sterilizing composition containing solvent, glutaraldehyde and salt with solvent to provide said sterilizing composition for utilization in said method.

* * * * *